United States Patent
Paul (10) Patent No.: US 6,180,099 B1
(45) Date of Patent: *Jan. 30, 2001

(54) METHOD OF USING IMMUNOGLOBULIN AND FIBER-CONTAINING COMPOSITIONS FOR HUMAN HEALTH

(75) Inventor: Stephen M. Paul, San Clemente, CA (US)

(73) Assignee: Metagenics, Inc., San Clemente, CA (US)

(*) Notice: Under 35 U.S.C. 154(b), the term of this patent shall be extended for 0 days.

This patent is subject to a terminal disclaimer.

(21) Appl. No.: 09/062,204

(22) Filed: Apr. 17, 1998

Related U.S. Application Data (63) Continuation of application No. 08/674,115, filed on Jul. 1, 1996, now Pat. No. 5,744,134, which is a continuation of application No. 08/437,316, filed on May 9, 1995, now Pat. No. 5,531,989, which is a continuation-in-part of application No. 08/331,140, filed on Oct. 28, 1994, now Pat. No. 5,531,988.

(51) Int. Cl.⁷ .......................... A01N 63/00; A61K 39/42; A61K 35/78; A61K 39/02; A61K 9/50; A61K 39/395

(52) U.S. Cl. .................. 424/93.4; 424/93.45; 424/161.1; 424/195.1; 424/234.1; 424/499; 424/500; 424/809

(58) Field of Search ................................ 424/93.4, 93.45, 424/161.1, 195.1, 234.1, 499, 500, 809, 246.1

(56) References Cited

U.S. PATENT DOCUMENTS

| | | |
|---|---|---|
| 4,091,117 | 5/1978 | Mutai et al. . |
| 4,377,569 | 3/1983 | Plymate . |
| 4,512,977 | 4/1985 | Lundy . |
| 4,784,852 | 11/1988 | Johansson . |
| 4,806,368 | 2/1989 | Reddy . |
| 4,816,252 | 3/1989 | Stott et al. . |
| 4,834,974 | 5/1989 | Stott et al. . |
| 4,977,137 | 12/1990 | Nichols et al. . |
| 4,994,442 | 2/1991 | Gil et al. . |
| 5,066,491 | 11/1991 | Stott et al. . |
| 5,145,698 | 9/1992 | Cajigas . |
| 5,240,909 | 8/1993 | Nitsche . |
| 5,330,756 | 7/1994 | Stewart et al. . |
| 5,413,765 | 5/1995 | Nanji . |
| 5,456,924 | 10/1995 | Bounous et al. . |
| 5,531,988 | 7/1996 | Paul . |
| 5,531,989 * | 7/1996 | Paul ..................................... 424/93.4 |
| 5,645,834 | 7/1997 | Cockrum . |
| 5,744,134 * | 4/1998 | Paul ..................................... 424/93.4 |
| 5,785,990 | 7/1998 | Langrehr . |
| 5,795,602 | 8/1998 | Craig et al. . |
| 5,846,569 | 12/1998 | Anderson et al. . |

FOREIGN PATENT DOCUMENTS

WO 99/64022   6/1998   (WO) .

OTHER PUBLICATIONS

Spectra Plex™ and Acidophilus Over Candida and Saimonella (consisting of 2 pages) (No Publication Date Available).

S. Tzipori, et al.; Remission of Diarrhoea Due to Cryptosporidiosis in an Immunodeficient Child Treated With Hyperimmune Bovine Colostrum; 1276–1277; 1986; British Medical Journal vol. 293.

E. B. Collins, et al.; Growth of Bifidobacteria in Milk and Preparation of Bifidobacterium Infantis for a Dietary Adjunct; 1376–1380; 1984; Journal of Dairy Science vol. 67.

N. Trenev, et al.; The Role of Probiotics in Geriatric and Infant Nutrition; 746–747; 1994; Townsend Letter for Doctors Bifadobacterium Adolescentis as Best Probiotic Selection; 1–8; 1992; Nutritional Consultants Group, Inc.

Advertisement "Intestinal Fortitude" Probioplex ™ Metagenics, Genetic Potential Through Nutrition (No Publication Date Available) (consisting of 2 pages).

Robert H. Yolken, et al.; Antibody to Human Rotavirus in Cow's Milk; 605–610; 1985; The New England Journal of Medicine vol. 312, No. 10.

Harold Brussow, et al.; Bovine Milk Immunoglobulins for Passive Immunity to Infantile Rotavirus Gastroenteritis; 982–986; 1987; Journal of Clinical Microbiology.

Helmut Hilper, et al; Use of Bovine Milk Concentrate Containing Antibody to Rotavirus to Treat Rotavirus Gastroenteritis in Infants; 158–166; 1987; The Journal of Infectious Diseases, vol. 156, No. 1.

Gustavo Boutlous et al.; The Immunoenhancing Property of Dietary Whey Protein Concentrate; 271–278; No. 11, No. 4 No Publication Date Available.

Carol O. Tacket, et al.; Protection by Milk Immunoglobulin Concentrate Against Oral Challenge with Enterotoxigenic *Escherichila Coli*; 1240–1243; 1988; The New England Journal of Medicine; vol. 318, No. 19.

O. deRham, et al.; Proteolysis of Bovine Immunoglobulins; 62–67; 1977; Int. Arcs Allergy App. Immun, 55.

(List continued on next page.)

Primary Examiner—Raymond Henley, III
(74) Attorney, Agent, or Firm—Clayton, Howarth & Cannon, P.C.

(57) ABSTRACT

A composition for restoring and maintaining gastrointestinal health comprises 40–60% by weight of an immunoglobulin composition comprising concentrated immunologically active immunoglobulins and 40–60% by weight of soluble dietary fiber selected from inulin, fructo-oligosaccharides, pectin, guar gum, and mixtures thereof. The immunoglobulin and fiber-containing composition can optionally contain one or more of a beneficial human intestinal microorganism, components of a non-immune natural defense system, an iron-sequestering molecule, and gluconic acid. Preferred beneficial human intestinal microorganisms include lactobacilli and bifidobacteria. The immunologically active immunoglobulins are preferably purified from bovine milk, milk products, or whey. Methods of use are also described.

75 Claims, 3 Drawing Sheets

OTHER PUBLICATIONS

Masashi Sato, et al.; Estimation of Circulating Immune Complexes Following Oral Challenge with Cow's Milk in Patients with IgA Nephropathy; 43–48; 1987; Nephron 47.

C. Cunningham–Rundles, et al; Dietary Bovine Antigens and Immune Complex Formation After Intravenous Immunoglobulin in Common Varied Immunodeficiency; 381–388; 1986; Journal of Clinical Immunology; vol. 6, No. 5.

C. Mietens, et al.; Treatment of Infantile *E. coli* Gastroenteritis with Specific Bovine anti–*E coli* Milk Immunoglobulines; 239–252; 1979, European Journal of Pediatrics, 132.

Thomas E. Besser, et al; Passive Immunity to Bovine Ratavirus Infection Associated with Transfer of Serum Antibody into the Intestinal Lumen; 2238–2243; 1988; Journal of Virology, vol. 62, No. 7.

Joseph C. Kolars, M.D. et al; Yogurt–an Autodigesting Source of Lacrose; 1–3; 1984; The New England Journal of Medicine; vol. 310, No. 1.

Marie–Hélène Coconnier, et al.; Protein–Mediated Adhesion of *Lactobacillus Acidophilus* BG2F04 on Human Enterocyte and Mucus–Secreting Cell Lines in Culture; 2034–2039; 1992; Applied and Environmental Microbiology, vol. 58, No. 6.

S.E. Gilliland, et al.; Factors to Consider when Selecting a Culture of *Lactobacillus acidophilus* as a Dietary Adjunct to Produce a Hypocholesterollemic Effect in Humans; 905–911; 1990, Journal of Dairy Science, vol. 73, No. 4.

L. Alm, The Effect of *Lactobacillus Acidophilus* Administration Upon the Survival of Salmonella in Randomly Selected Human Carriers; 13, 1983, Prog. Fd. Nurr. Sci., vol. 7.

S.E. Gilliland, et al.; Antagonistic Action of *Lactobacillus acidophilus* Toward Intestinal and Foodborne Pathogens in Associative Cultures; 820; 1977; Journal of Food Protection, vol. 40, No. 12.

Viki L. Hughes, MT, et al.; Microbiologic Characteristics of Lactobacillus Products Used for Colonization of the Vagina; 244, 246, 248; Obstetrics & Gynecology (No Publication Date Available).

Eileen Hilton, M.D., et al.; Ingestion of Yogurt Containing *Lactobacillus acidophilus* as prophylaxis for Candidal Vaginitis; 353–357; 1992; American College of Physicians, vol. 116, No. 5.

E. Collins, et al.; Inhibition of Candida Albicans by *Lactobacillus acidophilus;* 830–832; 1980; Journal of Dairy Science, vol. 63, No. 5.

E.G. Kleeman, et al.; Adherence of Lactobacillus Species to Human Fetal Intestinal Cells; 2063–2069; 1982; Journal of Dairy Science, vol. 65, No. 11.

V. Herbert, et al.; Contribution of the Microflora of the Small Intestine to the Vitamin B12 Nutriture of Man; 274–275; 1980, Nutrition Review, vol. 38, No. 8.

Clark Beck, M.D. et al.; Beneficial Effects of Administration of *Lactobacillus Acidophilus* in Diarrheal and other Intestinal Disorders; 522–530; 1961; The American Journal of Gastroenterology, vol. 35.

Alexander G. Schauss; *Lactobacillus Acidophilu:* Method of Action, Clinical Application, and Toxeity Data; 1–12; 1990; Journal of Advancement in Medicine (In Press).

Jerzy Meduski, M.D., Ph.D.; *Latobacillus acidophilus* Synopsis of its Attributes (consisting of 2 pages) (No Publication Date Available).

Ron Kohen, et al; Prevention of Oxidative Damage in the Rat Jejunal Mucosa by Pectin, *British J. of Nutrition;* 69, pp. 789–800, 1993.

Flourie B. et al; The effect of Pectin on Jejunal glucose absorption and unstirred layer thickness in normal man. *GUY,* 1984, Sep. 25(9) pp. 1936–1941.

Arbman, Gunnar MD, Cereal Fiber, Calcium and Colorectal Cancer, *Cancer,* vol. 69, No. 8, pp. 2042–2048, Apr. 15, 1992.

Jenkins, David et al; Dietary Fiber, Fiber Analogues and Glucose Tolerance, Importance of Viscosity; *British Medical Journal* 1, 1392–1394, May 27, 1978.

Sato H, et al; Antioxidant Activity of Synovial Fluid Hyaluronic Acid, and Two subcomponents of Hyaluronic Acid, *Arthritis And Rheumatism,* vol. 31, No. 1, Jan. 1988.

Reiter, B; Bacterial Inhibitors in Milk and other Secretions, with Special Reference to the Compliemnt, Transferring and Lactoperoxidase/Thiocyanate/Hydrogen Peroxide Systems. Inhibition and Inactiviation of Vegative Microbes, Academic Press, pp. 31–60, 1976.

Reiter, Bruno and Perraudin, J–P; Lactoperoxidase: Biological Functions: In Peroxidases in Chemistry and Biology, CRC Press, vol. #1, pp. 143–180, 1991.

Probioplex: Intestinal Fortitude, "sell sheet" published by Metagenics, Inc. (Jun. 1989).

\* cited by examiner

METHOD OF USING IMMUNOGLOBULIN AND FIBER-CONTAINING COMPOSITIONS FOR HUMAN HEALTH

RELATED APPLICATIONS

This application is a continuation of application Ser. No. 08/674,115, filed Jul. 1, 1996, now U.S. Pat. No. 5,744,134 issued on Apr. 28, 1998, which is a continuation of application Ser. No. 08/437,316, filed May 9, 1995, now U.S. Pat. No. 5,531,989, which is a continuation-in-part of application Ser. No. 08/331,140, filed Oct. 28, 1994, now U.S. Pat. No. 5,531,988.

BACKGROUND OF THE INVENTION

This invention relates to an immunoglobulin and fiber-containing composition and methods of use thereof for promoting gastrointestinal health. More particularly, the invention relates to a composition comprising an immunoglobulin preparation containing immunoglobulins that are capable of binding and inactivating foreign antigens such as pathogenic bacteria, viruses, fungi, and protozoa that are detrimental to gastrointestinal health; soluble dietary fiber that provides the advantages typically offered by dietary fibers with the additional advantages of not affecting blood glucose or insulin levels, being readily fermented by the intestinal microflora and promoting growth of certain beneficial intestinal microorganisms; and optionally one or more of the following: living intestinal bacteria that are beneficial for gastrointestinal health, lactoperoxidase and/or thiocyanate for strengthening a natural non-immune defense system, lactoferrin for inhibiting detrimental iron-catalyzed processes and harmful microorganisms, and gluconic acid for inhibiting growth of harmful bacteria and stimulating immune function.

Since the time of Hypocrites and throughout the Middle Ages, large doses of whey were prescribed by alchemists for treating many ailments, primarily acute septic conditions. Although it was not then known the reason that whey was useful for treating such conditions, recent studies have shown that whey contains antibodies or immunoglobulins capable of providing passive immunity against various pathogens and their toxic by-products. Antibodies or immunoglobulins are high mblecular weight proteins produced in the bodies of mature animals that enhance immunity to infection by bacteria, viruses, fungi, protozoa, and the like. Antibodies in human and bovine milk promote development of a healthy gastrointestinal tract and provide protection against infections by pathogenic microorganisms. These antibodies interfere with the process that allows such pathogenic microorganisms to adhere to and colonize the intestinal lining. Studies have shown that immunoglobulins from whey are particularly effective against viruses (e.g., rotavirus), bacteria (e.g., *E. coli, Vibrio cholerae, Salmonella*), fungi (e.g., Candida), and protozoa (e.g., Cryptosporidium).

Detectable levels of anti-rotavirus antibodies ($IgG_1$) have been found in raw and pasteurized milk. R. H. Yolken, Antibody to Human Rotavirus in Cow's Milk, 312 New Eng. J. Med. 605 (1985). The high temperatures used in processing infant formula, however, destroy all traces of naturally occurring $IgG_1$. Many infants develop gastroenteritis around 6 months of age, about the time they are weaned from breast milk and started on formula.

Since infants and young children are highly susceptible to gastroenteritis, treatment of acute diarrhea with concentrated immunoglobulins has been investigated. In one study, infants hospitalized with acute rotavirus gastroenteritis were treated with an immunoglobulin concentrate derived from rotavirus-immunized cows. H. Hilpert et al., *Use of Bovine Milk Concentrate containing Antibody to Rotavirus to Treat Rotavirus Gastroenteritis in Infants,* 156 J. Infect. Dis. 158 (1987). These infants showed significantly reduced duration of rotavirus excretion. Thus, bovine milk immunoglobulins provided passive immunity against rotavirus gastroenteritis in human infants.

A bovine milk immunoglobulin concentrate derived from *E. coli*-immunized cows has also been shown to inhibit colonization of enteropathic *E. coli* in affected infants. C. Mietens et al., *Treatment of Infantile E. Coli Gastroenteritis with Specific Bovine Anti-E. Coli Milk Immunoglobulins,* Eur. J. Pediatrics (1979). Stool samples showed a reduction in *E. coli* counts and the duration of diarrhea was shortened, demonstrating that this concentrate was effective in treating infantile diarrhea.

Inflammation of the gastrointestinal mucosa and diarrhea associated with Traveler's Diarrhea due to *E. coli* infection have been prevented by treatment with an immunoglobulin concentrate from bovine milk. C. Tacket et al., *Protection by Milk Immunoglobulin Concentrate against Oral Challenge with Enterotoxigenic Escherichia Coli,* 318 N. Engl. J. Med. 1240 (1988).

Immunoglobulins from bovine colostrum have been shown to be an effective treatment for diarrhea due to a pathogenic protozoan, Cryptosporidium. S. Tzipori et al., *Remission of Diarrhea Due to Cryptosporidiosis in an Immunodeficient Child Treated with Hyperimmune Bovine Colostrum,* 293 Br. Med. J. 1276 (1986). Immunodeficient individuals, particularly those with acquired immune deficiency syndrome (AIDS), are especially susceptible to Cryptosporidiosis.

Soluble fiber in the diet is well known for its salutary effects on gastrointestinal health. Such effects include providing bulk to the stool, decreasing the pH of the gastrointestinal tract, producing volatile fatty acids, decreasing intestinal transit time, and beneficially influencing various blood parameters. Dietary fiber has also been shown to have a beneficial effect on cholesterol and lipid metabolism that results in decreased serum cholesterol, triglycerides, and phospholipids and an improved (increased) HDL to LDL ratio. A study on laboratory animals showed that adding fiber to the diet decreases the incidence of bacterial translocation, i.e. crossing the intestinal barrier and entering systemic circulation. C. Palacio et al., Dietary Fiber: *Physiologic Effects and Potential Applications to Enteral Nutrition,* in Clinical Nutrition: Enteral and Tube Feeding (2d. ed., 1990). Nutritional and epidemiological studies have indicated that a general increase in the consumption of dietary fiber may play a role in preventing deleterious effects of oxygen free radicals that have been accused of being involved in such processes as aging, inflammation, and some disease processes. R. Kohen et al., *Prevention of Oxidative Damage in the Rat Jejunal Mucosa by Pectin,* 69 Br. J. Nutrition 789 (1993).

While prior art formulas as dietary supplements containing soluble dietary fiber or immunoglobulins are known and are generally suitable for their limited purposes, they possess certain inherent deficiencies that detract from their overall utility in restoring and maintaining gastrointestinal health. For example, a dietary supplement containing soluble dietary fiber without concentrated immunoglobulins lacks means for binding and inactivating foreign antigens such as pathogenic bacteria, viruses, fungi, and protozoa that can infect the gastrointestinal tract and are detrimental to the health thereof. Similarly, a dietary supplement containing concentrated immunoglobulins without soluble dietary fiber lacks means for providing bulk to the stool, decreasing the pH of the gastrointestinal tract, producing volatile fatty acids, decreasing intestinal transit time, beneficially influencing various blood parameters, beneficially influencing cholesterol and lipid metabolism, decreasing the incidence of bacterial translocation, preventing deleterious effects of oxygen free radicals, and favoring the growth of beneficial bacteria in the gastrointestinal tract. Further, such prior art formulas fail to provide living intestinal bacteria that are beneficial for gastrointestinal health by providing an inhibitory effect on the growth of pathogenic bacteria, reducing levels of toxic amines, and lowering the pH of the gastrointestinal tract. Further, prior art dietary supplements fail to provide components, such as lactoperoxidase and thiocyanate, that strengthen the body's natural non-immune defense system or LP-system. Moreover, these formulas do not contain inhibitors of detrimental iron-catalyzed processes and stimulators of immune function.

In view of the foregoing, it will be appreciated that a composition for improving and maintaining gastrointestinal health comprising an immunoglobulin preparation containing immunoglobulins that bind and inactivate pathogenic microorganisms in the gastrointestinal tract and soluble dietary fiber that provides the typical advantages of dietary fiber and additionally is low in calories, does not affect blood glucose or insulin levels, and favors the growth of beneficial bacteria in the gastrointestinal tract while at the same time inhibiting the growth of potentially pathogenic or harmful microorganisms would be a significant advancement in the art.

OBJECTS AND SUMMARY OF THE INVENTION

It is an object of the present invention to provide a composition for use as a dietary supplement that benefits human gastrointestinal health when administered orally.

It is also an object of the invention to provide a composition for use as a dietary supplement that, when ingested, is effective for treating ailments due to gastrointestinal pathogens such as bacteria, viruses, fungi, or protozoa.

It is another object of the invention to provide a composition for use as a dietary supplement that, when ingested, results in decreased serum cholesterol, triglycerides, and phospholipids and an increased HDL to LDL ratio.

It is still another object of the invention to provide a composition for use as a dietary supplement that aids in preventing deleterious effects of oxygen free radicals.

It is yet another object of the invention to provide a composition for use as a dietary supplement that bolsters the body's immune system and the natural non-immune system, the LP system.

It is a further object of the invention to provide a composition for use as a dietary supplement that inhibits detrimental iron-catalyzed processes in the body.

It is a still further object of the invention to provide a method of use for a dietary supplement composition that benefits human gastrointestinal health when administered orally.

These and other objects may be accomplished by providing an immunoglobulin and fiber-containing composition for use as a dietary supplement for restoring and maintaining gastrointestinal health comprising in percent by weight (a) about 40 to about 60% of an immunoglobulin composition comprising concentrated immunologically active immunoglobulins; and (b) about 40 to about 60% of soluble dietary fiber, wherein said fiber is a member selected from the group consisting of inulin, fructo-oligosaccharides, pectin, guar gum, and mixtures thereof. The immunoglobulin and fiber-containing composition can optionally contain about 0 to about 20% by weight of a beneficial human intestinal microorganism selected from the group consisting of lactobacilli and bifidobacteria. Preferably, the beneficial human intestinal microorganism is present in an amount in the range of about 0.1 to about 20% by weight, and more preferably of about 5 to about 10% by weight. The immunoglobulin and fiber-containing composition can also optionally contain one or more of the following ingredients:

| Ingredient | Ranges in Percent by Weight | |
|---|---|---|
| | Broad | Preferred |
| Lactoperoxidase | 0–0.0300% | 0.0001–0.0300% |
| Thiocyanate salt | 0–0.0500% | 0.0001–0.0500% |
| Lactoferrin | 0–0.1000% | 0.0001–0.1000% |
| Gluconic acid | 0–10% | 0.1–10% |

The beneficial human intestinal microorganism is preferably selected from the group consisting of *Lactobacillus acidophilus, L. bulgaricus, L. casei, L. fermentum, L. salivaroes, L. brevis, L. leichmannii, L. plantarum, L. cellobiosus, Bifidobacterium adolescentis, B. infantis, B. longum, B. thermophilum*, and *B. bifidum*. More preferably, the beneficial human intestinal microorganism is selected from *L. acidophilus* and *B. adolescentis*. A preferred strain of *L. acidophilus* is strain NCFM.

The immunoglobulin composition can also include a carrier. A preferred carrier comprises at least one member selected from the group consisting of a carbohydrate and a lipid, wherein the carbohydrate is capable of being an energy source for a beneficial human intestinal microorganism and the lipid aids in reconstitution of the immunoglobulin composition. A preferred carbohydrate is maltodextrin, and a preferred lipid is lecithin. Preferably, the immunoglobulin composition is purified from a source selected from the group consisting of milk, milk products, and whey, with a bovine source also being preferred.

A method of restoring and maintaining gastrointestinal health comprises the step of orally administering an effective amount of an immunoglobulin and fiber-containing composition for promoting gastrointestinal health comprising in percent by weight (a) about 40 to about 60% of an immunoglobulin composition comprising concentrated immunologically active immunoglobulins; and (b) about 40 to about 60% of soluble dietary fiber, wherein the fiber is a member selected from the group consisting of inulin, fructo-oligosaccharides, pectin, guar gum, and mixtures thereof.

BRIEF DESCRIPTION OF THE DRAWINGS

FIG. 2 shows growth curves for Candida (•) cultured alone and for a mixed culture of Candida (♦) and *L.*

*acidophilus* NCFM (♦) also containing an immunoglobulin composition according to the present invention.

DETAILED DESCRIPTION OF THE INVENTION

Figure 1:
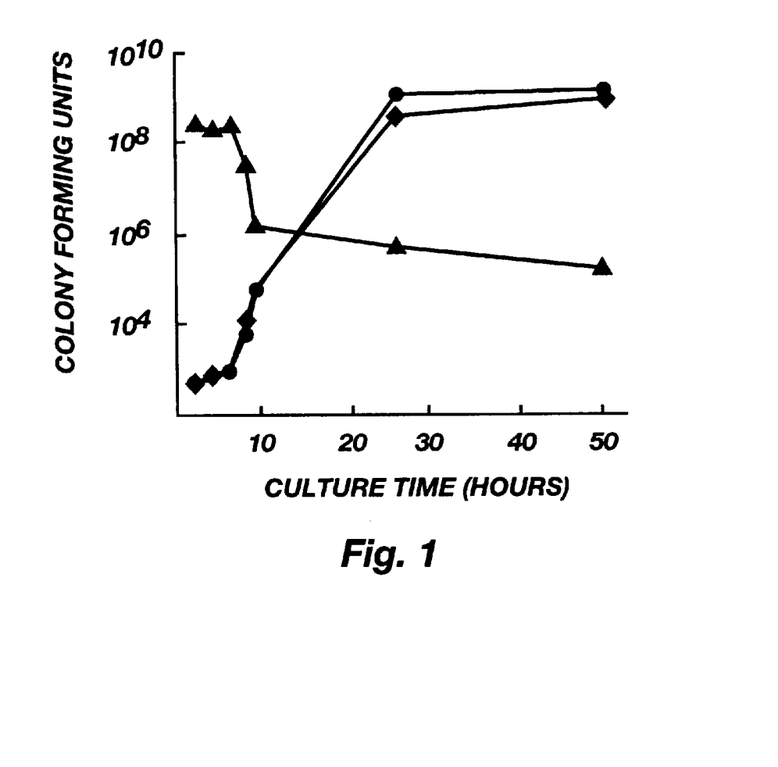
FIG. 1 shows growth curves for Candida (•) cultured alone and for a mixed culture of Candida (♦) and *L. acidophilus* NCFM (▲).
Figure 2:
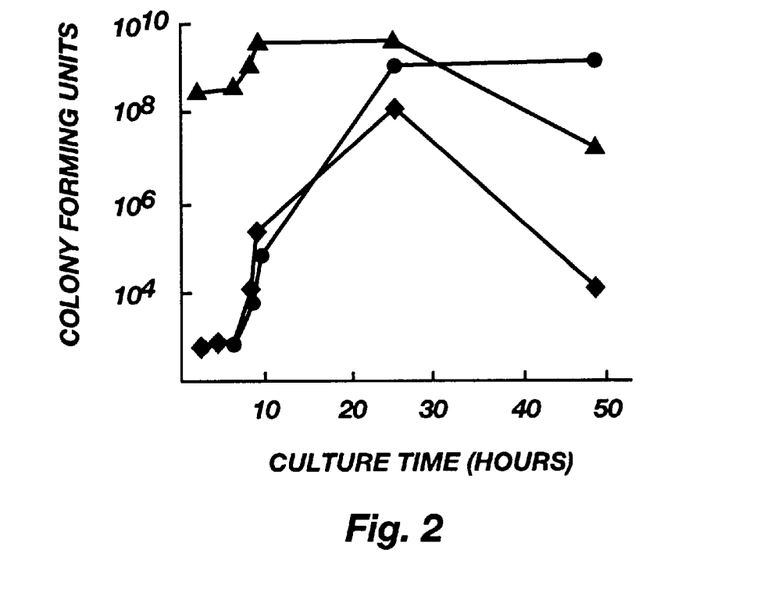
Figure 3:
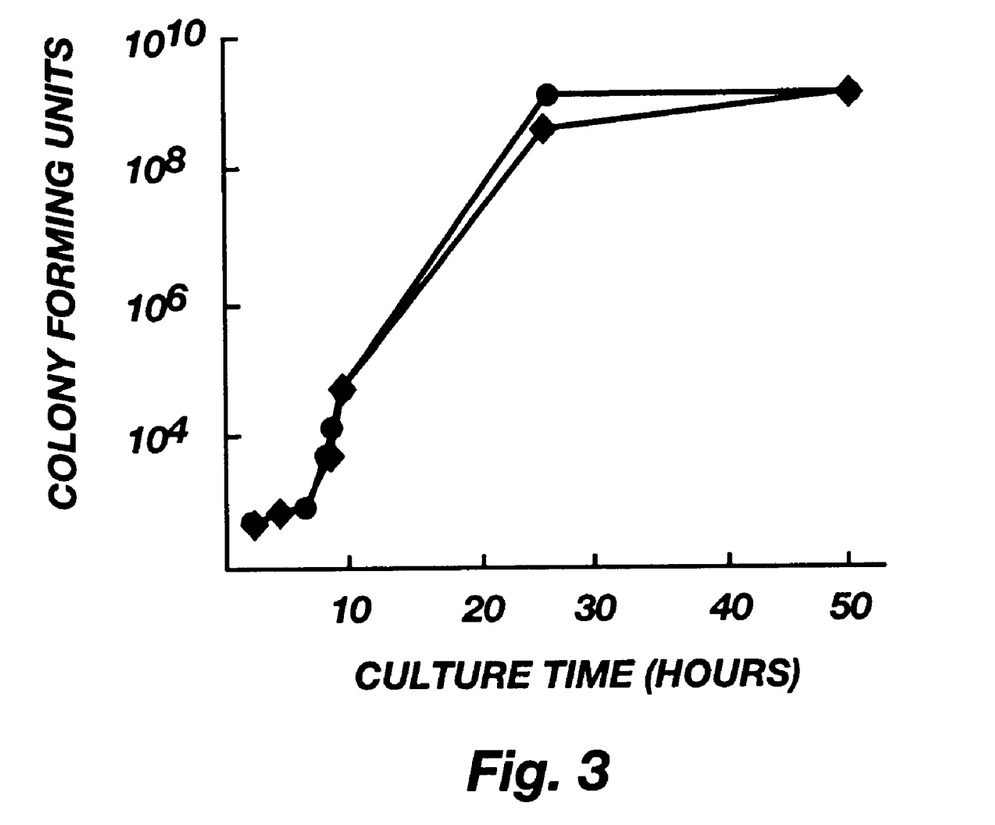
FIG. 3 shows growth curves for Candida (•) cultured alone and for Candida (♦) cultured in the presence of an equal amount of immunoglobulin composition as in FIG. 2.
Figure 4:
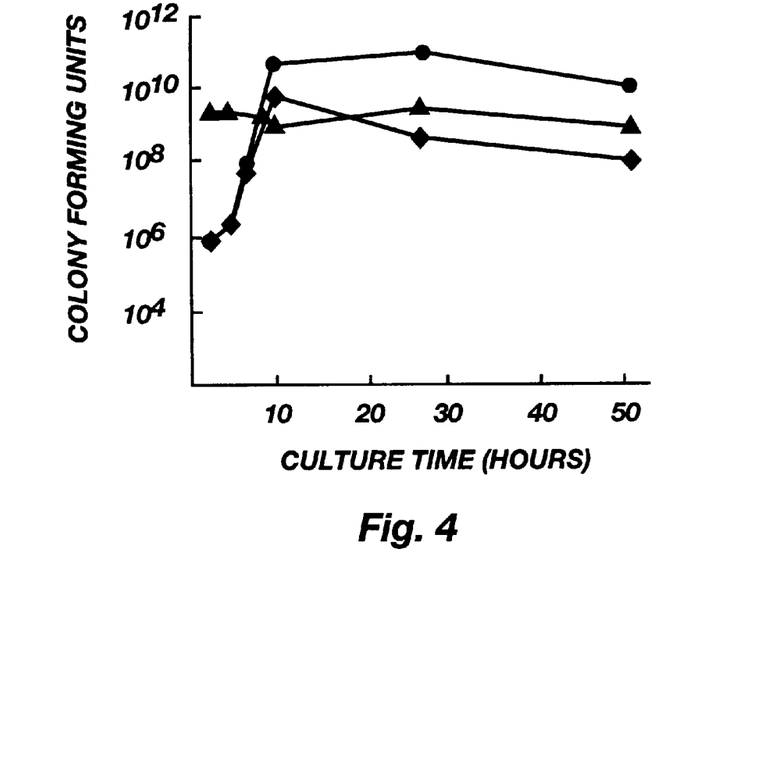
FIG. 4 shows growth curves for *S. typhimurium* (•) cultured alone and for a mixed culture of *S. typhimurium* (♦) and *L. Acidophilus* NCFM (▲).
Figure 5:
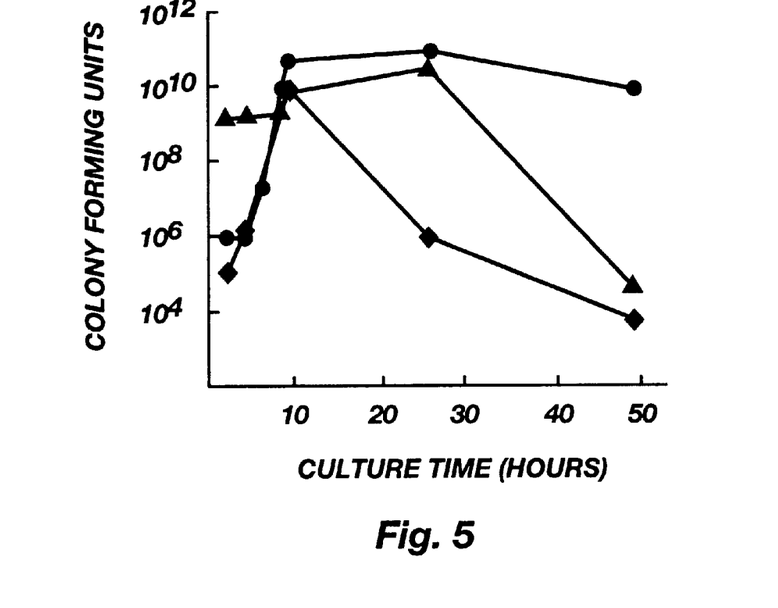
FIG. 5 shows growth curves for *S. typhimurium* (•) cultured alone and for a mixed culture of *S. typhimurium* (♦) and *L. Acidophilus* NCFM (▲) also containing an immunoglobulin composition according to the present invention.

Before the present composition and methods of use are disclosed and described, it is to be understood that this invention is not limited to the particular examples, process steps, and materials disclosed herein as such process steps and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition containing "a microorganism" includes a mixture of two or more microorganisms, reference to "an immunoglobulin" includes reference to two or more of such immunoglobulins, and reference to "a concentrate" includes reference to a mixture of two or more of such concentrates.

In describing and claiming the present invention, the following terminology will be used in accordance with the definitions set out below.

As used herein, "immunoglobulin composition" means a composition comprising an effective amount of immunologically active immunoglobulins. Preferably, these are present as concentrated immunologically active immunoglobulins. One such immunoglobulin composition is sold under the trademark "PROBIOPLEX" by Metagenics, Inc. (San Clemente, Calif.). PROBIOPLEX contains (1) about 55–60 parts by weight of an immunoglobulin concentrate from bovine whey wherein at least about 7% by weight of the total solids in the concentrate is immunologically active immunoglobulins, (2) about 35–40 parts by weight of a mixture of carbohydrates including rice maltodextrin and lactose, and (3) about 5–10 parts by weight of lipid including lecithin. Thus, at least about 3.6% by weight of the total PROBIOPLEX composition comprises immunologically active immunoglobulins. The carbohydrates and lipids function as inert carriers for the immunoglobulins. The rice maltodextrin can function further as an energy source for beneficial microorganisms with which the immunoglobulin composition can be mixed in accordance with the present invention. The lecithin aids in dispersion of the powder form of the immunoglobulin composition when reconstituted with water or other liquid. Although PROBIOPLEX contains ingredients other than concentrated immunologically active immunoglobulins, these other ingredients are optional components of the invention. What is required is that the immunoglobulin composition contain an "effective amount" of immunologically active immunoglobulins that are preferably present in concentrated form.

As used herein, "beneficial human intestinal microorganism" means an organism of microscopic size, such as a bacterium, that inhabits the human intestine and exerts a beneficial effect on the gastrointestinal health of an individual in which it resides. Preferred beneficial human intestinal microorganisms according to the present invention include bacteria of the genera Lactobacillus and Bifidobacterium. A more preferred lactobacillus is *L. acidophilus*, with *L. acidophilus* strain NCFM being most preferred, and a more preferred bifidobacterium is *B. adolescentis*. Other lactobacilli that are beneficial to gastrointestinal health include *L. bulgaricus, L. casei, L. fermentum, L. salivaroes, L. brevis, L. leichmannii, L. plantarum*, and *L. cellobiosus*. Other bifidobacteria that are beneficial to gastrointestinal health include *B. infantis, B. longum, B. thermophilum*, and *B. bifidum*.

As used herein, "effective amount" means an amount necessary to achieve a selected result. For example, an effective amount of an immunoglobulin and fiber-containing composition useful for reducing the titer of a selected pathogenic microorganism in the gastrointestinal tract would be an amount that achieves the selected result of reducing the titer of the microorganism. Such an amount can be readily determined without undue experimentation by a person of ordinary skill in the art.

As used herein, "thiocyanate salt" means a nutritionally acceptable salt of the thiocyanate anion, such as sodium thiocyanate, potassium thiocyanate, ammonium thiocyanate, and mixtures thereof.

The advantages of soluble dietary fiber have been briefly reviewed above. Inulin is one such fiber that is composed of a mixture of oligomers and polymers of fructose. Inulin is a storage carbohydrate found in many plants including onion, asparagus, artichoke, and many cereals. Chicory root and Jerusalem artichoke each contain about 70% by weight of inulin. Inulin has been an important food in Europe for many years and is currently being used as a source of dietary fiber, for replacing fat in the diet, and for promoting growth of beneficial bacteria in the intestine. In the U.S., inulin is added to all types of noodles. It has a moderately sweet taste, is highly soluble, and is a frequent replacement for sugar in many foods. Medically, inulin is the substance of choice to study renal clearance and impaired kidney function.

Fructo-oligosaccharides (FOS) are another type of soluble dietary fiber. FOS is widely distributed in nature and is found in honey, beer, onion, asparagus, Chinese chive, banana, maple sugar, oats, and Jerusalem artichoke.

Upon ingestion, both inulin and FOS are hydrolyzed to a negligible extent as they pass through the mouth, stomach, and small intestine. In the large intestine, they are readily fermented by the intestinal microflora. These carbohydrates are metabolized by the bacteria into short chain fatty acids, mainly acetic, propionic, butyric, and lactic acids. As a consequence of this fermentation, a considerable amount of bacterial mass is produced, which increases stool wet weight. The short chain fatty acids are absorbed by the large intestine and are further metabolized in the liver. This allows the body to recover some energy from inulin and FOS, although the efficiency of energy conversion is markedly lower than with other carbohydrates. This phenomenon underlies the low calorie content of fructans and dietary fibers.

Inulin and FOS are used as a source of energy in the intestinal tract mainly by bacteria in the genus Bifidobacterium. H. Hidaka et al., *Effects of Fructooligosaccharides on Intestinal Flora and Human Health*, 5 Bifidobacteria Microflora 37–50 (1986). When inulin and FOS are administered in the diet, the bifidobacteria increase significantly, becoming the predominant bacteria in the intestinal population, and the clostridia, which are a measure of potentially pathogenic microorganisms, are significantly reduced. As will be discussed in more detail below, bifidobacteria are human intestinal bacteria that provide beneficial effects on gastrointestinal health. Other important groups of bacteria in the mixed population in the intestines, such as Fusobacterium, Lactobacillus, and aerobic bacteria, are not significantly affected by the administration of inulin and FOS. H. Hidaka et al., *Effects of Fructooligosaccharides on Intestinal Flora and Human Health,* 5 Bifidobacteria Microflora 37–50 (1986).

It has been shown, A. Hata, *The Influence of Neosugar on the Lipid Metabolism of Experimental Animals,* Proc. 1st Neosugar Res. Conference, Tokyo (1982), that fructo-oligosaccharides (FOS) in the diet of experimental animals cause reduction of blood sugar, serum cholesterol, triglycerides, and phospholipids; significant improvement in the HDL/LDL ratio; an increase in free fatty acids; and significant decreases in total cholesterol in lipedemia cases.

It has also been shown, H. Hadaka et al., *Effects of Fructooligosaccharides on Intestinal Flora and Human Health,* 5 Bifidobacteria Microflora 37–50 (1986), that administration of fructo-oligosaccharides (FOS) enhances growth of the bifidobacteria population in the intestine, suppresses production of putrefactive factors, improves blood lipid levels in hyperlipidemia patients, and provides relief from constipation.

Therefore, at least the following positive effects are obtained by addition of inulin and/or fructo-oligosaccharides (FOS) to a composition for use as a dietary supplement according to the present invention: reduction of intestinal disorders, enhancement of a balanced intestinal microflora, and remediation of constipation.

Other preferred dietary fibers according to the present invention include pectin and guar gum. Pectin is a highly water soluble, noncellulosic polysaccharide fiber extracted from the primary cell walls of plants. Rich sources of pectin include lemon and orange rinds, which contain about 30% by weight of this polysaccharide. Pectin occurs naturally as a partial methyl ester of $\alpha$-(1→4) linked D-polygalacturonate sequences interrupted with (1→2)-L-rhamnose residues. Pectins are used as gelling and thickening agents in food technology and as an antidiarrheal in veterinary medicine. Guar gum is produced from the ground endosperms of *Cyamopsis tetragonolobus,* a legume cultivated in India as a livestock feed. The water soluble fraction, which comprises about 85% of guar gum and is known as guaran, consists of linear chains of (1→4)-$\beta$-D-mannopyranosyl units with $\alpha$-D-galactopyranosyl units attached by (1→6) linkages. The ratio of D-galactose to D-mannose is 1:2. Guar gum has 5 to 8 times the thickening power of starch and, thus, is used as a thickener in foods, as a binder and disintegrating agent in tablet formulations, and in pharmaceuticals and cosmetics.

Pectin and guar gum have several beneficial effects on the gastrointestinal tract, such as maintaining the morphology of intestinal villi, increasing lipase activity in the small bowel, delaying gastric emptying time, increasing intestinal transit time, and promoting increased fecal production of short chain fatty acids. It is believed that pectin and guar gum in the diet lower blood glucose and serum cholesterol levels, B. Flourie et al., The Effect of Pectin on Jejunal Glucose Absorption and Unstirred Layer Thickness in Normal Man, 25 Gut 1936 (1984). Also, dietary fiber supplementation with pectin or guar gum has also been found to significantly suppress the incidence of colon cancer. G. Arbman, *Cereal Fiber, Calcium and Colorectal Cancer,* 69 Cancer 2042 (1992). Studies with whole apples show that fiber (pectin) in the fruit reduces the insulin response to the sugar in the fruit and prevents "rebound" hypoglycemia. D. Jenkins et al., *Dietary Fiber, Fiber Analogues and Glucose Tolerance, Importance of Viscosity,* 1 Br. Med. J. 1392 (1978). Further, pectin and guar gum are readily degraded by bacterial fermentation in the colon, probably because of their high water solubility.

Moreover, pectin and guar gum are also thought to prevent oxidative damage in the gastrointestinal tract. Oxygen free radicals are involved in many deleterious processes including aging, inflammation, and some disease processes. The gastrointestinal mucosa is exposed to oxidants produced within the lumen and in the epithelial cells. Potential sources of luminal oxidants include ingested food, catalase-negative bacteria, and cigarette smoke and other pollutants. The production of reactive free radicals during metabolism of dietary fat can explain some the biological damage such as loss of membrane function, inactivation of membrane-bound enzymes, and inactivation of essential molecules located inside the cell. Other tests have shown that a large amount of fat in the diet can be a presumptive carcinogen. H. Hidaka et al., *Effects of Fructooligosaccharides on Intestinal Flora and Human Health,* 5 Bifidobacteria Microflora 37–50 (1986). Apart from these carcinogenic changes, still other injuries associated with free radicals include ulcerative diseases, inflammation, and ischemic bowel disease. Pectin and guar gum prevent oxidative damage in various ways. They directly scavenge intestinal oxidants. Further, pectin can act as a chelating agent of loosely bound transition metals in the lumen. Moreover, pectin also reacts directly to prevent spontaneous dismutation of superoxide radicals and thus prevents the formation of hydrogen peroxide.

As reviewed above, immunoglobulin concentrates from milk contain immunologically active immunoglobulins that are capable of binding pathogenic microorganisms such as bacteria, viruses, fungi, and protozoa. Such immunoglobulin concentrates can be prepared from any starting material containing sufficient concentrations of immunologically active immunoglobulins, such as milk, whey, blood, and the like. An economically viable source of such immunoglobulins is the whey byproduct of the cheese making process. It has been estimated that approximately 85 million metric tons of whey are created annually as a byproduct of cheese production worldwide. About 34 million metric tons of whey are not economically utilized, and thus are discarded. The whey byproduct of cheese making, therefore, presents an inexpensive and ready source of immunoglobulins.

Numerous techniques are known to exist for producing dry concentrated protein extract from whey. This protein extract is commonly referred to as whey protein concentrate or "WPC." Such protein extraction and concentration techniques have been primarily concerned with preserving the food qualities of the WPC, such as taste, flavor, and solubility. Although these techniques are useful for producing food products, they almost universally destroy or substantially reduce the immunological activity of immunoglobulins in the concentrate by exposing the raw milk, whey, or protein concentrate to (1) excessive thermal (time and temperature) conditions, (2) excessive bacterial activity, or (3) excessive enzymes added in processing or resulting from bacterial activity.

Methods have been developed for separating immunologically active immunoglobulins from raw milk. U.S. Pat.

Nos. 4,816,252 and 4,834,974 describe such methods, which are illustrative of methods that can be used for preparing an immunologically active immunoglobulin concentrate according to the present invention. Raw milk is first flash pasteurized to control microbial activity in the milk without significantly diminishing the immunological activity of the immunoglobulins in the milk. Next, the milk is exposed to an appropriate cheese starter culture, such as a lactobacillus, at carefully controlled temperatures and for limited times to achieve a selected degree of curd formation without significantly affecting the immunological activity of the immunoglobulins. The whey is then separated from the cheese curd and transferred to a clarifier or separator under carefully controlled conditions to remove fat and casein particles. The clarified whey is then subjected to ultrafiltration to remove or substantially reduce the amounts of small proteins, salts, and other non-protein materials in the retained protein concentrate or retentate. Ultrafiltration can be performed in stages to optimize purification of the immunoglobulins. Optionally, other concentration and purification steps, such as reverse osmosis and ion exchange chromatography, can then be used to further improve the purity and concentration of the immunoglobulin concentrate while maintaining the immunological activity thereof. The immunoglobulin concentrate is then dried through conventional freeze-drying or spray drying methods. The resulting dry immunoglobulin concentrate can then be stored at room temperature. At least about 7% of the total solids of immunoglobulin concentrates prepared by these methods comprise immunologically active immunoglobulins. When ultrafiltration and ion exchange chromatography are both used in the purification procedure, the proportion of immunologically active immunoglobulins as a percentage of total solids can be increased to at least about 50%. Repeated ion exchange chromatography steps can further increase the proportion of immunologically active immunoglobulins as a percentage of total solids. U.S. Pat. Nos. 4,816,252 and 4,834,974 are hereby incorporated herein by reference as illustrative of methods for purifying immunologically active immunoglobulin concentrate. The present invention is not limited to these methods, however, and any method of purifying and concentrating immunologically active immunoglobulins from milk, whey, or another suitable source is to be considered within the scope of the invention as long as an effective amount of immunologically active immunoglobulins is obtained in the "immunoglobulin composition." Bovine milk and bovine whey are preferred sources of immunoglobulins, but other species of animal could also be used.

Certain bacteria have also been shown to be beneficial to human gastrointestinal health. The intestinal flora of the human gut contains some $100 \times 10^9$ viable bacteria, representing 100 or more different species. The major bacteria can be roughly divided into three groups: (a) lactic acid bacteria, including lactobacilli, bifidobacteria, and streptococci; (b) anaerobic bacteria; and (c) aerobic bacteria.

Bacteria of the genus Lactobacillus have been used for several hundred years for treating various illnesses. Lactobacilli found in the human intestinal tract include *L. acidophilus, L. casei, L. fermentum, L. salivaroes, L. brevis, L. leichmannii, L. plantarum*, and *L. cellobiosus*. In recent years, *L. acidophilus* has been shown to be exceptionally useful in treating conditions such as antibiotic-induced imbalances in the gastrointestinal microflora, hypercholesterolemia, vaginal infections, *E. coli* infection, oral contraceptive failure, depressed immunity, cancerous tumors, chronic granulomatous disease, and lactose indigestion. A. G. Shauss, *Method of Action, Clinical Application, and Toxicity Data*, 3 J. Advancement Med. 163 (1990). In vitro studies have shown *L. acidophilus* to have an inhibitory effect on the growth of pathogenic bacteria such as *Campylobacter pylori, Staphylococcus aureus, Pseudomonas aeruginosa*, and *Sarcina lutea*. K. M. Shahani et al., Natural Antibiotic Activity of Lactobacillus Acidophilus and Bulgaricus, 11 Cultured Dairy Products J. 14 (1976).

The beneficial effect of *L. acidophilus* is further illustrated by preliminary evidence that *L. acidophilus* inhibits the toxic activities of bacteria in patients with chronic kidney failure. M. L. Simenhoff et al., Biomodulation of Uremic Pathophysiology in Man, abstract presented at Am. Soc. of Nephrology Meeting, Baltimore, 1992. Such patients often have toxic levels of amines in their blood due to bacterial overgrowth in the small bowel. Consumption of high levels of freeze dried bacteria drastically reduces levels of these toxic amines. These results demonstrate the ability of *L. acidophilus* to exert a positive effect on the microflora of the intestines.

It has also been shown that the activities of fecal bacterial enzymes thought to play a role in conversion of procarcinogens to carcinogens, such as beta-glucuronidase, nitroreductase, and azoreductase, were reduced 2- to 4-fold in subjects taking *L. acidophilus* supplements. B. R. Goldin & L. S. Gorbach, *The Effect of Milk and Lactobacillus Feeding on Human Intestinal Bacterial Enzyme Activity*, 39 Amer. J. Clin. Nutr. 756 (1984). These results suggest that dietary supplementation with *L. acidophilus* may reduce the risk of developing colon cancer.

Bifidobacteria are also known to exert a beneficial influence on human health. These bacteria exert antimicrobial activity in the human intestine by producing lactic acid and acetic acid as a result of carbohydrate metabolism. These acids lower the intestinal pH, thereby inhibiting overgrowth of gastrointestinal pathogens. Therapeutic applications of bifidobacteria are indicated for the management of diarrhea and constipation, and the management of hepatic encephalopathy with hyperammonemia. Additional benefits include the production of B vitamins and breakdown of carcinogenic N-nitrosamines.

Bifidobacteria constitute the predominant microorganisms in the fecal flora of week-old breast-fed infants, making up 85–99% of the bacterial population. Upon weaning or upon the occurrence of perturbations such an infection, vaccination, a sudden change in diet, and even the weather can upset the balance of microorganisms in the gastrointestinal tract of these babies. Bifidobacteria can also be significantly reduced in elderly people due to a reduction of secreted gastric juices. The bifidobacterial population in adults is much more stable, however changes in diet, administration of antibiotics, exposure to gamma radiation or X-rays, disease, stress, and other disturbances can result in overgrowth of potentially pathogenic bacteria, decrease in beneficial bacteria (lactobacilli and bifidobacteria), and a resulting imbalance in the gastrointestinal flora. Hyperproliferation of harmful bacteria in the gut is associated with various forms of diarrhea, susceptibility to systemic infections, constipation, vague and acute abdominal symptoms, fatigue, dyspepsia, and presence of carcinogenic metabolites. Reestablishment of a normal balance of gastrointestinal flora can be accelerated, and such normal balance maintained, with dietary administration of lactobacilli and/or bifidobacteria.

Lactobacilli and bifidobacteria produce organic acids that reduce intestinal pH and thereby inhibit the growth of acidsensitive undesirable bacteria. Lactobacilli produce lactic acid, hydrogen peroxide, and possibly acetic and benzoic acids. Bifidobacteria produce short chain fatty acids (SCFA) such as acetic, propionic, and butyric acids, as well as lactic and formic acids. The most plentiful short chain fatty acid produced by bifidobacteria is acetic acid, which has a wide range of antimicrobial activities against yeasts, molds, and other bacteria. Additionally, short chain fatty acids support normal gastrointestinal function by increasing colonic blood flow, stimulating pancreatic enzyme secretion, promoting sodium and water absorption, and potentiating intestinal mucosal growth. Bifidobacteria are also known to deconjugate bile salts to free bile acids, which are more inhibitory to susceptible bacteria than are the conjugated forms. Further, lactobacilli and bifidobacteria are able to produce other antimicrobial substances, such as bacteriocins, that inhibit the growth and proliferation of harmful bacteria in the gut.

In human and animal tissues, peroxidases form part of a natural non-immune defense system and also play a role in protecting against microbial invasion of mucous membranes. Peroxidases occur in various exocrine gland secretions including salivary, lachrymal, bronchial, nasal, and intestinal secretions and in milk. Milk peroxidases, known as lactoperoxidases (LP) are the predominant enzymes in bovine milk. LP has no intrinsic antibacterial activity, however, together with hydrogen peroxide and thiocyanate anion it forms a potent natural antibacterial system, the so-called lactoperoxidase or LP system (for review see B. Reiter, Bacterial Inhibitors in Milk and Other Secretions with Special Reference to the Complement, Transferrin and Lactoperoxidase/Thiocyanate/Hydrogen Peroxide Systems, in Inhibition and Inactivation of Vegetative Microbes 31–60 (1976); B. Reiter & J. -P. Perraudin, Lactoperoxidase: Biological Functions, in 1 Peroxidases in Chemistry and Biology 143–180 (1991). The antibacterial effect of the LP system is mediated by the generation of short-lived oxidation products of thiocyanate anion (SCN), mainly the hypothiocyanate ion (OSCN). LP is a highly active enzyme, and very low concentrations are sufficient to establish an effective system. A wide range of bacterial species is affected by the LP system. Gram-negative bacteria generally are killed or their growth inhibited. Gram-positive bacteria usually are more resistant, however, and in general only their growth is inhibited. The LP system can also affect certain viruses, yeasts, and molds.

The thiocyanate anion is widely distributed in animal and human tissues, body-fluids, and secretions. It is found in the mammary, salivary, and thyroid glands, in the stomach and kidneys, in synovial, cerebral, and spinal fluid, and in lymph and plasma. The major dietary sources of thiocyanate ion are vegetables such as cabbage, cauliflower, and turnip, which are rich in glucosinolates that yield thiocyanate ion upon hydrolysis.

The activity of the LP system arises from an LP-catalyzed reaction in which hydrogen peroxide oxidizes thiocyanate ion (SCN) to form the hypothiocyanate ion (OSCN). The hypothiocyanate ion then oxidizes sulfhydryl groups in vital metabolic enzymes and other proteins of the microorganisms. The mechanisms of antimicrobial activity of the LP system result in damage to bacterial membranes and inhibition of essential transport mechanisms, such as those involving glucose and amino acids, and inhibition of synthesis of nucleic acids and proteins, including vital metabolic enzymes such as those involved in glycolysis.

Microorganisms inhibited by the LP system include a number of Gram-positive bacteria, including species of Staphylococcus and Streptococcus, and some Gram-negative species, e.g., $E.\ coli$, $Salmonella$, $Pseudomonas$. Some lactic acid bacteria, e.g. lactobacilli and bifidobacteria, are unaffected by the LP system because they contain a "reversal enzyme" called NAD(P)-OSCN-oxidase reductase, which prevents the antimicrobial activity of the LP system.

Lactoperoxidase is a highly active enzyme, and very low concentrations, along with low concentrations of hydrogen peroxide and thiocyanate ion, are sufficient to obtain an effective system. Hydrogen peroxide is known to be produced in many species of lactobacilli, and thiocyanate ion is widely distributed in animal and human tissues, body fluids, and secretions.

Advantages of the LP system include a greater antimicrobial efficacy and a wider spectrum of activity than existing preservatives. Also, the active antimicrobial agents of the LP system (OSCN and HOSCN) disappear from food after processing, thus providing a safe, long-lasting food preservative without the presence of the active preservative agents. Further, the LP system acts in synergy with other preservatives, thus increasing the efficacy of such other preservatives. Moreover, the LP system has a very low level of toxicity.

Lactoferrin is an iron-binding protein present in milk. For example, bovine milk contains about 200 mg/l of lactoferrin, and human milk and colostrum contain about 2–4 g/l and 6–8 g/l of lactoferrin, respectively. The affinity of lactoferrin for iron is very high, e.g. about 300 times that of the iron-transporting protein, transferrin, in blood plasma. A lactoferrin molecule binds one ferric ion ($Fe^{3+}$) by means of a bicarbonate-dependent reaction.

The high affinity for iron enables the use of lactoferrin for inhibiting iron-catalyzed processes, such as generation of free hydroxyl radicals, lipid peroxidation, and growth of microorganisms. Most microorganisms need iron for growth. Lactoferrin is able to inhibit the growth of such microorganisms by depriving them of iron. Lactoferrin is bacteriostatic to a wide range of microorganisms, including Gram-negative bacteria with a high iron requirement and some Gram-positive bacteria. Lactic acid bacteria, such as lactobacilli and bifidobacteria, have a low iron requirement and, in general, are not affected by lactoferrin. Although lactoferrin is primarily bacteriostatic, heat-treated lactoferrin is bactericidal. Heat-treated lactoferrin is easily obtained by heating lactoferrin at acidic pH.

Lactoferrin has been demonstrated in in vitro and in vivo tests to be effective against a variety of microorganisms, including $E.\ coli$, $Staphylococcus\ epidermidis$, $Streptococcus\ pneumoniae$, and $Candida\ albicans$, while at the same time promoting the growth of bifidobacteria. Lactoferrin retains iron at low pH and can pass through the acid environment of the stomach and enter the intestine unaltered.

As described above, various indigestible saccharides, such as FOS, have been developed for promoting the growth of bifidobacteria. Another substance that promotes the growth of bifidobacteria is gluconic acid and its salts (gluconates) It has been shown in in vitro fermentation tests that gluconate is utilized selectively by bifidobacteria as an energy source. H. Sato et al., $Antioxidant\ Activity\ of\ Synovial\ Fluid,\ Hyaluronic\ Acid,\ and\ Two\ Subcomponents\ of\ Hyaluronic\ Acid$, 31 Arthritis & Rheumatism (1988). In addition to promoting the growth of bifidobacteria, gluconic acid, like other organic acids, also suppresses the growth of certain harmful bacteria, such as $Clostridium\ perfringens$. Test results have further shown that ingested gluconic acid and gluconates are not absorbed in the small intestine, but instead are able to reach the large intestine where they can be utilized as an energy source by bifidobacteria. Sato et al., *Antioxidant Activity of Synovial Fluid, Hyaluronic Acid, and Two Subcomponents of Hyaluronic Acid,* 31 Arthritis & Rheumatism (1988).

In accordance with a preferred embodiment of the present invention, there is provided an immunoglobulin and fiber-containing composition for use as a dietary supplement. The formulation preferably includes a mixture of an immunoglobulin composition and a soluble dietary fiber selected from the group consisting of inulin, fructo-oligosaccharide, pectin, guar gum, and mixtures thereof in optimal ratios to restore and maintain good gastrointestinal health.

In its most fundamental form, the immunoglobulin and fiber-containing formulations of the present invention include a mixture of about 40 to about 60% by weight of an immunoglobulin composition comprising concentrated immunologically active immunoglobulins and about 40 to about 60% by weight of soluble dietary fiber selected from the group consisting of inulin, fructo-oligosaccharides, pectin, guar gum, and mixtures thereof.

It is also preferable that the formulation contain a beneficial human intestinal microorganism for restoring and maintaining good gastrointestinal health. The beneficial human intestinal microorganism is preferably a member selected from the group consisting of lactobacilli and bifidobacteria. Preferred lactobacilli include *L. acidophilus, L. bulgaricus, L. casei, L. fermentum, L. salivaroes, L. brevis, L. leichmannii, L. plantarum,* and *L. cellobiosus. L. acidophilus* is more preferred and L. acidophilus strain NCFM is most preferred. Preferred bifidobacteria include *B. adolescentis, B. infantis, B. longum, B. thermophilum,* and *B. bifidum. B. adolescentis* is more preferred. Such beneficial human intestinal bacteria can be added to the base formulation in an amount in the range of about 0 to about 20% by weight, preferably about 0.1 to about 20% by weight, and more preferably about 5 to about 10% by weight.

It is also preferable that the formulation contain one or more additives for enhancing the activity of the body's non-immune defense system known as the LP system. Such additives can be added to the base formulation, with or without the presence of optional ingredients, in the following concentrations: lactoperoxidase in an amount in the range of about 0 to about 0.0300% by weight and thiocyanate salt in an amount in the range of about 0 to about 0.0500% by weight. Preferably, lactoperoxidase is present in an amount in the range of about 0.0001 to about 0.0300% by weight, and thiocyanate salt is present in an amount in the range of about 0.0001 to about 0.0500% by weight.

It is also preferable that the formulation contain additional optional ingredients for inhibiting the growth of harmful intestinal microorganisms and/or promoting the growth of beneficial human intestinal microorganisms, such as bifidobacteria. Such additives can be added to the base formulation, with or without the presence of other optional ingredients, in the following concentrations: lactoferrin in an amount in the range of about 0 to about 0.1000% by weight and gluconic acid, its nutritionally acceptable salts, or mixtures thereof in an amount in the range of about 0 to about 10% by weight. Preferably, lactoferrin is present in an amount in the range of about 0.0001 to about 0.1000% by weight, and gluconic acid, its nutritionally acceptable salts, or mixtures thereof in an amount in the range of about 0.1 to about 10% by weight.

The composition is preferably manufactured in powder form by agglomerating the dry, raw material ingredients in a suitable agglomerator so as to result in a finished product having a uniform composition with the precise proportions of the components. The bacteria are prepared, for example, by culturing in a rich medium such as LB, J. Miller, Experiments in Molecular Genetics, Cold Spring Harbor Laboratory, Cold Spring Harbor, N.Y. (1972), until the late log phase of growth is reached. The bacteria are then concentrated and lyophilized according to standard methods. The agglomerated material is then packaged in a suitable container. Just prior to consumption, the dry composition is reconstituted with water, juice, or the like to result in a smooth liquid composition that can be consumed orally. If desired, the composition can be formulated in liquid form. The preferred daily dosage of the formula ranges from about 5 to about 15 grams based on the powdered composition. The daily dosage can be ingested in a single serving or divided into various servings and taken at intervals. Preferably, the composition of the present invention is taken between meals.

The composition of the present invention can be used for maintaining gastrointestinal health as well as for treating diarrhea, constipation, and other types of gastrointestinal distress due to infection with pathogenic microorganisms such as *E. coli,* Salmonella, Candida, rotavirus, and Cryptosporidium by orally administering an effective amount of the composition. The effective amount will vary depending on the size and age of the individual, whether the selected effect is to maintain gastrointestinal health or to restore gastrointestinal health from distress due to infection with a pathogenic microorganism, the particular pathogenic microorganism involved, and the like. A person skilled in the art can routinely determine such an effective amount. The dry ingredients of the composition are stirred into water or juice, and the resulting suspension is taken by mouth. Preferably, dosage is in the range of about 20 to about 400 mg/kg of body weight. More preferably, dosage is in the range of about 70 to about 215 mg/kg of body weight. Doses of the bacteria and immunoglobulin-containing composition can be divided, wherein two or more administrations of divided doses are used to deliver a complete dose. Multiple doses can also be administered, but it is recommended that daily consumption be limited to 1 to 3 doses.

EXAMPLE

The following formulas represent specific embodiments of the invention. These may be prepared in the manner indicated above by blending together the stated raw ingredients in an agglomerator so as to result in a finished product having uniform composition with the precise proportions of the components as indicated. The agglomerated material is then packaged in a suitable container. In the preferred embodiment, the formula comprises the following ingredients stated in amounts by weight:

| Formulation A | |
|---|---|
| Inulin | 50% |
| Immunoglobulin comp. | 50% |
| Formulation B | |
| Inulin | 40% |
| Immunoglobulin comp. | 40% |
| *L. acidophilus* NCFM | 20% |

-continued

| | |
|---|---|
| Formulation C | |
| Pectin | 40% |
| Immunoglobulin comp. | 60% |
| Formulation D | |
| Guar Gum | 20% |
| Pectin | 30% |
| Immunoglobulin comp. | 40% |
| B. adolescentis | 10% |
| Formulation E | |
| Inulin | 30% |
| FOS | 15% |
| Immunoglobulin comp. | 49.72% |
| L. acidophilus NCFM | 2.5% |
| B. adolescentis | 2.5% |
| Lactoperoxidase | 0.03% |
| Sodium thiocyanate | 0.05% |
| Lactoferrin | 0.1% |
| Gluconic acid | 0.1% |
| Formulation F | |
| Inulin | 40% |
| Pectin | 9.98% |
| Immunoglobulin comp. | 40% |
| B. adolescentis | 10% |
| Lactoperoxidase | 0.02% |
| Formulation G | |
| Inulin | 10% |
| FOS | 10% |
| Pectin | 10% |
| Guar Gum | 10% |
| Immunoglobulin comp. | 52.95% |
| L. acidophilus NCFM | 7% |
| Potassium thiocyanate | 0.05% |
| Formulation H | |
| Inulin | 50.9% |
| Immunoglobulin comp. | 40% |
| B. adolescentis | 9% |
| Lactoferrin | 0.1% |
| Formulation I | |
| Inulin | 42% |
| Immunoglobulin comp. | 40% |
| B. adolescentis | 8% |
| Sodium gluconate | 10% |
| Formulation J | |
| Inulin | 20% |
| FOS | 20% |
| Pectin | 4.44% |
| Guar Gum | 1% |
| Immunoglobulin comp. | 40% |
| B. adolescentis | 10% |
| Lactoperoxidase | 0.01% |
| Ammonium thiocyanate | 0.05% |
| Sodium gluconate | 4.5% |
| Formulation K | |
| FOS | 36% |
| Pectin | 3.5% |
| Guar Gum | 2.5% |
| Immunoglobulin comp. | 42% |
| L. acidophilus NCFM | 10% |
| Lactoferrin | 0.01% |
| Gluconic acid | 5.99% |
| Formulation L | |
| Inulin | 40% |
| Immunoglobulin comp. | 40% |
| B. adolescentis | 10% |
| Lactoperoxidase | 0.0001% |
| Sodium thiocyanate | 0.0001% |
| Lactoferrin | 0.0001% |
| Gluconic acid | 10% |

I claim:

1. A method of restoring and maintaining gastrointestinal health comprising orally administering about 20 to about 400 mg of an immunoglobulin- and fiber-containing composition per kg of body weight comprising:
   (a) about 8 to about 240 mg of an immunoglobulin composition comprising concentrated immunologically active immunoglobulins per kg of body weight; and
   (b) about 8 to about 240 mg of soluble dietary fiber per kg of body weight.

2. The method of claim 1 wherein said fiber is a member of the group consisting of inulin, fructo-oligosaccharides, pectin, guar gum, and mixtures thereof.

3. The method of claim 1 wherein said immunoglobulin composition comprises at least about 3.6% by weight of immunologically active immunoglobulins.

4. The method of claim 1 wherein said immunoglobulin- and fiber-containing composition comprises:
   (a) about 28 to about 129 mg of an immunoglobulin composition comprising concentrated immunologically active immunoglobulins per kg of body weight; and
   (b) about 28 to about 129 mg of soluble dietary fiber per kg of body weight.

5. The method of claim 1 wherein said immunoglobulin- and fiber-containing composition further comprises about 0.02 to about 80 mg of a beneficial human intestinal microorganism per kg of body weight.

6. The method of claim 5 wherein said beneficial human intestinal microorganism is a member selected from the group consisting of lactobacilli and bifidobacteria.

7. The method of claim 5 wherein said immunoglobulin- and fiber-containing composition comprises about 0.07 to about 43 mg of a beneficial human intestinal microorganism per kg of body weight.

8. The method of claim 5 wherein said immunoglobulin- and fiber-containing composition further comprises about 0.02 to about 200 μg of thiocyanate salt and about 0 to about 120 μg of lactoperoxidase per kg of body weight.

9. The method of claim 6 wherein said immunoglobulin- and fiber-containing composition further comprises about 0.02 to about 200 μg of thiocyanate salt and about 0 to about 120 μg of lactoperoxidase per kg of body weight.

10. The method of claim 9 wherein said immunoglobulin- and fiber-containing composition comprises about 0.02 to about 120 μg of lactoperoxidase per kg of body weight.

11. The method of claim 1 wherein said immunoglobulin- and fiber-containing composition further comprises about 0.02 to about 400 μg of lactoferrin and about 0 to about 40 mg of a member selected from the group consisting of gluconic acid, its nutritionally acceptable salts, and mixtures thereof per kg of body weight.

12. The method of claim 5 wherein said immunoglobulin- and fiber-containing composition further comprises about 0.02 to about 400 μg of lactoferrin and about 0 to about 40 mg of a member selected from the group consisting of gluconic acid, its nutritionally acceptable salts, and mixtures thereof per kg of body weight.

13. The method of claim 8 wherein said immunoglobulin- and fiber-containing composition further comprises about 0.02 to about 400 μg of lactoferrin and about 0 to about 40 mg of a member selected from the group consisting of gluconic acid, its nutritionally acceptable salts, and mixtures thereof per kg of body weight.

14. The method of claim 9 wherein said immunoglobulin- and fiber-containing composition further comprises about 0.02 to about 400 μg of lactoferrin and about 0 to about 40 mg of a member selected from the group consisting of gluconic acid, its nutritionally acceptable salts, and mixtures thereof per kg of body weight.

15. The method of claim 14 wherein said immunoglobulin- and fiber-containing composition comprises about 0.02 to about 40 mg of a member selected from the group consisting of gluconic acid, its nutritionally acceptable salts, and mixtures thereof per kg of body weight.

16. The method of claim 6 wherein said beneficial human intestinal microorganism is a member selected from the group consisting of *Lactobacillus acidophilus, L. bulgaricus, L. casei, L. fermentum, L. salivaroes, L. brevis, L. Leichmannii, L. plantarum*, and *L. cellobiosus*.

17. The method of claim 16 wherein said beneficial human intestinal microorganism is of Lactobacillus acidophilus.

18. The method of claim 17 wherein said *Lactobacillus acidophilus* is strain NCFM.

19. The method of claim 6 wherein said beneficial human intestinal microorganism is a member selected from the group consisting of *Bifidobacterium adolescentis, B. infantis, B. longum, B. thermophilum*, and *B. bifidum*.

20. The method of claim 19 wherein said beneficial human intestinal microorganism is a member selected from the group consisting of *Bifidobacterium adolescentis*.

21. The method of claim 1 wherein said immunoglobulin composition further comprises a carrier.

22. The method of claim 21 wherein said carrier comprises at least one member selected from the group consisting of a carbohydrate and a lipid, wherein said carbohydrate is capable of being an energy source for a beneficial human intestinal microorganism and said lipid aids in reconstitution of said immunoglobulin composition.

23. The method of claim 22 wherein said carbohydrate comprises maltodextrin and said lipid comprises lecithin.

24. The method of claim 21 wherein said immunoglobulin composition is purified from a source selected from the group consisting of milk, whey products, and whey.

25. The method of claim 24 wherein said source is bovine.

26. A method for bolstering the immune system comprising orally administering about 20 to about 400 mg of an immunoglobulin- and fiber-containing composition per kg of body weight comprising:
  (a) about 8 to about 240 mg of an immunoglobulin composition comprising concentrated immunologically active immunoglobulins per kg of body weight; and
  (b) about 8 to about 240 mg of soluble dietary fiber per kg of body weight.

27. The method of claim 26 wherein said fiber is a member of the group consisting of inulin, fructooligosaccharides, pectin, guar gum, and mixtures thereof.

28. The method of claim 26 wherein said immunoglobulin composition comprises at least about 3.6% by weight of immunologically active immunoglobulins.

29. The method of claim 26 wherein said immunoglobulin- and fiber-containing composition comprises:
  (a) about 28 to about 129 mg of an immunoglobulin composition comprising concentrated immunologically active immunoglobulins per kg of body weight; and
  (b) about 28 to about 129 mg of soluble dietary fiber per kg of body weight.

30. The method of claim 26 wherein said immunoglobulin- and fiber-containing composition further comprises about 0.02 to about 80 mg of a beneficial human intestinal microorganism per kg of body weight.

31. The method of claim 30 wherein said beneficial human intestinal microorganism is a member selected from the group consisting of lactobacilli and bifidobacteria.

32. The method of claim 30 wherein said immunoglobulin- and fiber-containing composition comprises about 0.07 to about 43 mg of a beneficial human intestinal microorganism per kg of body weight.

33. The method of claim 30 wherein said immunoglobulin- and fiber-containing composition further comprises about 0.02 to about 200 µg of thiocyanate salt and about 0 to about 120 µg of lactoperoxidase per kg of body weight.

34. The method of claim 31 wherein said immunoglobulin- and fiber-containing composition further comprises about 0.02 to about 200 µg of thiocyanate salt and about 0 to about 120 µg of lactoperoxidase per kg of body weight.

35. The method of claim 34 wherein said immunoglobulin- and fiber-containing composition comprises about 0.02 to about 120 µg of lactoperoxidase per kg of body weight.

36. The method of claim 26 wherein said immunoglobulin- and fiber-containing composition further comprises about 0.02 to about 400 µg of lactoferrin and about 0 to about 40 mg of a member selected from the group consisting of gluconic acid, its nutritionally acceptable salts, and mixtures thereof per kg of body weight.

37. The method of claim 30 wherein said immunoglobulin- and fiber-containing composition further comprises about 0.02 to about 400 µg of lactoferrin and about 0 to about 40 mg of a member selected from the group consisting of gluconic acid, its nutritionally acceptable salts, and mixtures thereof per kg of body weight.

38. The method of claim 33 wherein said immunoglobulin- and fiber-containing composition further comprises about 0.02 to about 400 µg of lactoferrin and about 0 to about 40 mg of a member selected from the group consisting of gluconic acid, its nutritionally acceptable salts, and mixtures thereof per kg of body weight.

39. The method of claim 34 wherein said immunoglobulin- and fiber-containing composition further comprises about 0.02 to about 400 µg of lactoferrin and about 0 to about 40 mg of a member selected from the group consisting of gluconic acid, its nutritionally acceptable salts, and mixtures thereof per kg of body weight.

40. The method of claim 39 wherein said immunoglobulin- and fiber-containing composition comprises about 0.02 to about 40 mg of a member selected from the group consisting of gluconic acid, its nutritionally acceptable salts, and mixtures thereof per kg of body weight.

41. The method of claim 31 wherein said beneficial human intestinal microorganism is a member selected from the group consisting of *Lactobacillus acidophilus, L. bulgaricus, L. casei, L. fermentum, L. salivaroes, L. brevis, L. Leichmannii, L. plantarum*, and *L. cellobiosus*.

42. The method of claim 41 wherein said beneficial human intestinal microorganism is of *Lactobacillus acidophilus*.

43. The method of claim 42 wherein said *Lactobacillus acidophilus* is strain NCFM.

44. The method of claim 31 wherein said beneficial human intestinal microorganism is a member selected from the group consisting of *Bifidobacterium adolescentis, B. infantis, B. longum, B. thermophilum*, and *B. bifidum*.

45. The method of claim 44 wherein said beneficial human intestinal microorganism is a member selected from the group consisting of *Bifidobacterium adolescentis*.

46. The method of claim 26 wherein said immunoglobulin composition further comprises a carrier.

47. The method of claim 46 wherein said carrier comprises at least one member selected from the group consisting of a carbohydrate and a lipid, wherein said carbohydrate is capable of being an energy source for a beneficial human intestinal microorganism and said lipid aids in reconstitution of said immunoglobulin composition.

48. The method of claim 47 wherein said carbohydrate comprises maltodextrin and said lipid comprises lecithin.

49. The method of claim 26 wherein said immunoglobulin composition is purified from a source selected from the group consisting of milk, whey products, and whey.

50. The method of claim 49 wherein said source is bovine.

51. A method for bolstering the immune system of an individual comprising orally administering an immunoalobulin- and fiber-containing composition comprising:

(a) about 8 to about 240 mg of an immunoglobulin composition comprising concentrated immunologically active immunoglobulins per kg of body weight; and (b) about 8 to about 240 mg of soluble dietary fiber per kg of body weight.

52. The method of claim 51 wherein said fiber is a member of the group consisting of inulin, fructo-oligosaccharides, pectin, guar gum, and mixtures thereof.

53. The method of claim 51 wherein said immunoglobulin composition comprises at least about 3.6% by weight of immunologically active immunoglobulins.

54. The method of claim 51 wherein said immunoglobulin- and fiber-containing composition comprises:

(a) about 28 to about 129 mg of the immunoglobulin composition comprising concentrated immunologically active immunoglobulins per kg of body weight; and (b) about 28 to about 129 mg of soluble dietary fiber per kg of body weight.

55. The method of claim 51 wherein said immunoglobulin- and fiber-containing composition further comprises about 0.02 to about 80 mg of a beneficial human intestinal microorganism per kg of body weight.

56. The method of claim 55 wherein said beneficial human intestinal microorganism is a member selected from the group consisting of lactobacilli and bifidobacteria.

57. The method of claim 55 wherein said immunoglobulin- and fiber-containing composition comprises about 0.07 to about 43 mg of a beneficial human intestinal microorganism per kg of body weight.

58. The method of claim 55 wherein said immunoglobulin- and fiber-containing composition further comprises about 0.02 to about 200 µg of thiocyanate salt and about 0 to about 120 µg of lactoperoxidase per kg of body weight.

59. The method of claim 56 wherein said immunoglobulin- and fiber-containing composition further comprises about 0.02 to about 200 µg of thiocyanate salt and about 0 to about 120 µg of lactoperoxidase per kg of body weight.

60. The method of claim 59 wherein said immunoglobulin- and fiber-containing composition comprises about 0.02 to about 120 µg of lactoperoxidase per kg of body weight.

61. The method of claim 51 wherein said immunoglobulin- and fiber-containing composition further comprises about 0.02 to about 400 µg of lactoferrin and about 0 to about 40 mg of a member selected from the group consisting of gluconic acid, its nutritionally acceptable salts, and mixtures thereof per kg of body weight.

62. The method of claim 55 wherein said immunoglobulin- and fiber-containing composition further comprises about 0.02 to about 400 µg of lactoferrin and about 0 to about 40 mg of a member selected from the group consisting of gluconic acid, its nutritionally acceptable salts, and mixtures thereof per kg of body weight.

63. The method of claim 58 wherein said immunoglobulin- and fiber-containing composition further comprises about 0.02 to about 400 µg of lactoferrin and about 0 to about 40 mg of a member selected from the group consisting of gluconic acid, its nutritionally acceptable salts, and mixtures thereof per kg of body weight.

64. The method of claim 59 wherein said immunoglobulin- and fiber-containing composition further comprises about 0.02 to about 400 µg of lactoferrin and about 0 to about 40 mg of a member selected from the group consisting of gluconic acid, its nutritionally acceptable salts, and mixtures thereof per kg of body weight.

65. The method of claim 104 wherein said immunoglobulin- and fiber-containing composition comprises about 0.02 to about 40 mg of a member selected from the group consisting of gluconic acid, its nutritionally acceptable salts, and mixtures thereof per kg of body weight.

66. The method of claim 56 wherein said beneficial human intestinal microorganism is a member selected from the group consisting of Lactobacillus acidophilus, L. bulgaricus, L. casei, L. fermentum, L. salivaroes, L. brevis, L. Leichmannii, L. plantarum, and L. cellobiosus.

67. The method of claim 66 wherein said beneficial human intestinal microorganism is of Lactobacillus acidophilus.

68. The method of claim 67 wherein said Lactobacillus acidophilus is strain NCFM.

69. The method of claim 56 wherein said beneficial human intestinal microorganism is a member selected from the group consisting of Bifidobacterium adolescentis, B. infantis, B. longum, B. thermophilum, and B. bifidum.

70. The method of claim 69 wherein said beneficial human intestinal microorganism is a member selected from the group consisting of Bifidobacterium adolescentis.

71. The method of claim 51 wherein said immunoglobulin composition further comprises a carrier.

72. The method of claim 71 wherein said carrier comprises at least one member selected from the group consisting of a carbohydrate and a lipid, wherein said carbohydrate is capable of being an energy source for a beneficial human intestinal microorganism and said lipid aids in reconstitution of said immunoglobulin composition.

73. The method of claim 72 wherein said carbohydrate comprises maltodextrin and said lipid comprises lecithin.

74. The method of claim 51 wherein said immunoglobulin composition is purified from a source selected from the group consisting of milk, whey products, and whey.

75. The method of claim 74 wherein said source is bovine.

* * * * *